US00PP33315P2

(12) United States Plant Patent
Hansen

(10) Patent No.: US PP33,315 P2
(45) Date of Patent: Aug. 3, 2021

(54) ***PHLOX* PLANT NAMED 'ROSE QUARTZ'**

(50) Latin Name: ***Phlox* hybrid**
Varietal Denomination: Rose Quartz

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,228

(22) Filed: Nov. 19, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ... A01H 5/02; A01H 5/00; A01H 6/70; A01H 6/36
See application file for complete search history.

(56) References Cited

PUBLICATIONS

North Branch Nursery, Inc. Perennial Inventory Sep. 16, 2020, retrieved on Mar. 15, 2021, retrieved from the Internet at http://www.northbranchnursery.com/wp-content/uploads/perennial.pdf, pp. 1 and 31. (Year: 2020).*

* cited by examiner

*Primary Examiner* — June Hwu

(57) ABSTRACT

A unique cultivar of Hybrid Creeping *Phlox* named 'Rose Quartz' characterized by vigorous, dense, spreading, multi-stemmed, winter-hardy habit with short, bright-green, shiny, linear leaves. Small flowers begin in mid-spring and continuing for up to six weeks in cooler weather conditions, on heavily-branched peduncles and completely cover the plant in peak season. Petals are rose-pink with a lighter center and a moderate notch and the tips of the petals. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Rose Quartz'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Dec. 1, 2019. Subsequently, the new plant was advertised in the "Walters Gardens 20-21 Catalog" by Walters Gardens, Inc. released on May 20, 2020. The claimed plant was first sold to Pleasant View Gardens/Proven Winners® on Jun. 15, 2020 by Walters Gardens, Inc., who obtained the plant and all information relating thereto, from the inventor. No plants of *Phlox* 'Rose Quartz' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Creeping *Phlox* plant known as *Phlox* 'Rose Quartz' and will be referred to hereafter by its cultivar name, 'Rose Quartz', or the "new plant". The new plant was hybridized by the inventor at a wholesale perennial nursery in Zeeland, Mich. on Apr. 27, 2015 as a cross between *Phlox subulata* 'Drummond's Pink' (not patented) as the female or seed parent and the proprietary, unreleased, hybrid known by the breeder code 14-260-5 (not patented) as the male or pollen parent. The new plant passed initial evaluation on the spring of 2017 and was assigned the breeder code 15-130-1 through the remaining evaluation process. 'Rose Quartz' was first asexually propagated by stem cuttings in the greenhouses at the same nursery in Zeeland, Mich. in the summer of 2017. The unique characteristics of the new plant have been found to be reproducible and stable in successive generations of asexually propagated plants, and the resultant plants have been found to be identical to the original selection.

BRIEF SUMMARY OF THE PLANT

*Phlox* 'Rose Quartz' is unique from all other Creeping *Phlox* known to the inventor. The nearest comparison plants known to the inventor include: the female and male parents, 'Ruby Riot' copending U.S. Plant patent application Ser. No. 16/974,227, 'Pink Sprinkles' copending U.S. Plant patent application Ser. No. 16/974,294, 'Majestic Magenta' U.S. Plant patent application Ser. No. 16/974,098 'Barseventy-four' U.S. Plant Pat. No. 23,564 and 'Rocky Road Magenta' U.S. Plant Pat. No. 31,485. The female parent, 'Drummond's Pink', has lighter pink flowers with rounded rather than emarginate petal apices. The male parent, 14-260-5, has flower petals that are more notched in the apex, the flower color is more lavender, the habit is taller, and the leaves broader. 'Ruby Riot' has a similar habit with flowers of reddish-pink and darker eyes. 'Pink Sprinkles' has larger flowers that are lighter baby pink in color. 'Majestic Magenta' has flowers that are more purplish-red hue. 'Barseventyfour' has a similar flower color, but the backs of the flowers and the front eye are darker. 'Rocky Road Magenta' has a smaller habit with slower spreading growth rate and the flowers vibrant magenta-purple flowers with small dark-purple eye.

*Phlox* 'Rose Quartz' differs from all other *Phlox* known to the inventor in the following repeatedly observed traits in combination:

1. Semi-vigorous plants of dense spreading habit, spreading by rooting stems, producing short, clean, bright-green, shiny, linear leaves;
2. Multiple heavily-branched stems produce branched panicles;
3. Flower beginning in mid-spring and continuing for up to six weeks, in cool conditions, completely covering plant at peak flowering;
4. Large flowers of rose-pink developing lighter eye and with moderate notches at the tip of the petals;
5. Plant is able to withstand dry conditions once established.

BRIEF DESCRIPTION OF THE DRAWINGS

The photographs of the new plant demonstrate the unique traits of *Phlox* 'Rose Quartz' and the overall appearance of the plant at two-years-old growing in a full-sun trial garden in Zeeland, Mich. The colors in the drawings are as accurate as reasonably possible with color reproductions. Variation in ambient light spectrum; source and direction may cause the appearance of minor variation in color.

DETAILED BOTANICAL DESCRIPTION

Figure 1:
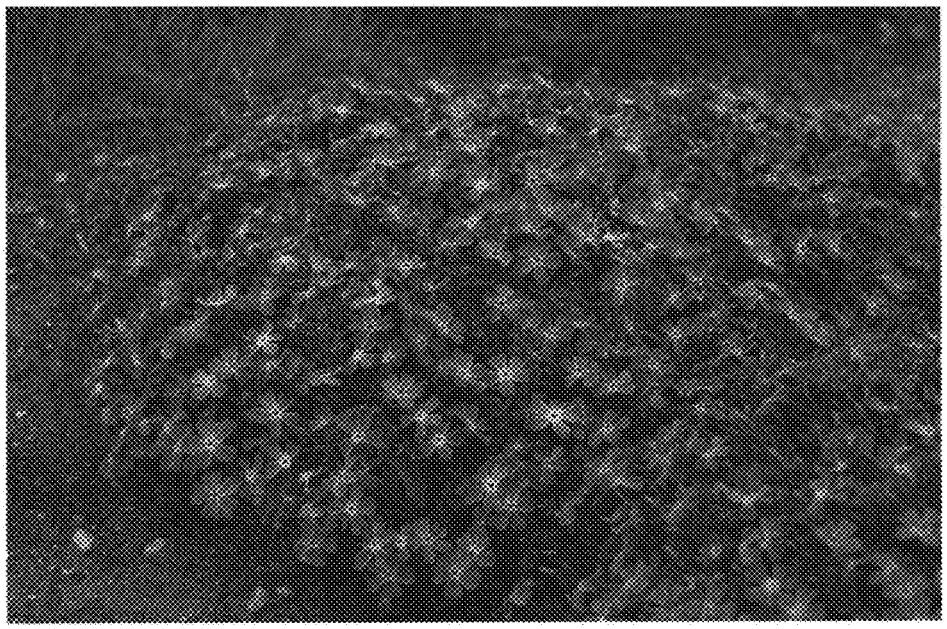
FIG. 1 shows a landscape habit view of the new plant in peak flower.
Figure 2:
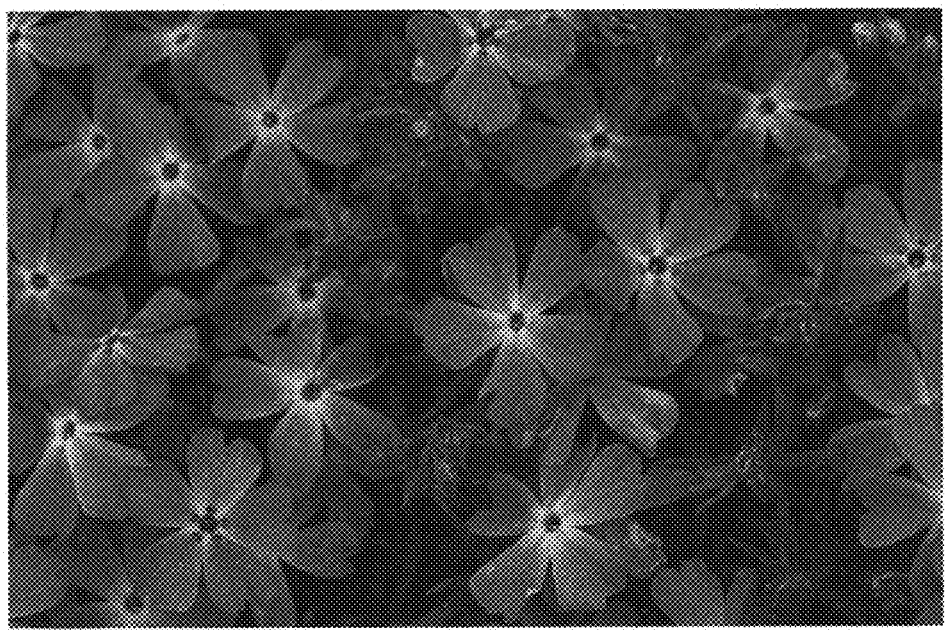
FIG. 2 shows a close-up of the flowers.

The following descriptions and color references are based on the 2015 edition of The Royal Horticultural Society Colour Chart except where common dictionary terms are used. *Phlox* 'Rose Quartz' has not been observed under all possible environments. The phenotype may vary slightly with different growing environments such as temperature, light, fertility, soil pH, moisture and maturity levels, but without any change in the genotype. The following observations and size descriptions are based on two-year-old plants in a partially shaded greenhouse or a full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Drummond's Pink', male or pollen parent is 14-260-5 which is a cross between *Phlox bifida* 'Topnotch' (not patented) and a proprietary selection of *Phlox* x *procumbens* (not patented);

Plant habit: Winter-hardy, evergreen herbaceous perennial; short, dense, producing about 50 stiff, highly-branched prostrate stems; foliage and stems to 16.0 cm tall and 48.0 cm wide; flowering to 19.0 cm tall and 52.0 cm wide;

Propagation: Stem cuttings; rooting in about 2 weeks;

Time to produce finished crop in 3.8 liter pots: About 10 to 12 weeks; vigorous;

Root: Fibrous and freely branching; color creamy white to tan depending on soil type;

Leaves: Simple; opposite; linear to subulate; apex narrowly acute to apiculate; base truncate, clasping; margin ciliolate; glabrous and moderately lustrous both adaxial and abaxial; to about 25.0 mm long by about 2.5 mm wide and 0.3 mm thick at base, average about 22.5 mm long and 2.0 mm wide and 0.3 mm thick at base;

Leaf color: Adaxial expanding nearest RHS 138A and mature adaxial nearest RHS 137A, abaxial expanding nearest RHS 146B and mature abaxial nearest RHS 137A; winter adaxial color variable, proximally and portions protected from strong sun nearest RHS 137C and distally where exposed to high sun nearest a blend between RHS 187A and RHS 182C; winter abaxial color variable, in portions not exposed to high sun nearest a blend between RHS 137C and RHS 146C and where exposed to high sun nearest RHS 137C with light blush of nearest RHS 187A;

Foliage fragrance: None detected;

Veins: Pinnate; not conspicuous adaxial and abaxial;

Vein color: Same color as surrounding leaf;

Petiole: Leaves sessile;

Stems: Cylindrical; flexible; wiry; prostrate; puberulent when expanding; highly compound branching; to about 68.0 mm long and 2.0 mm diameter near base;

Stem color: Young expanding stems nearest RHS 145C, proximal and older stems nearest RHS 156B;

Nodes: About 5.0 mm apart proximally; distally about 1.0 mm apart;

Node color: Color nearest RHS 156B proximally and nearest RHS 145B distally;

Inflorescence: Upright to outwardly; about 3.5 cm long and 5.3 cm wide; average of 3.5 flowers;

Flowers: Perfect; salverform; mostly flat faced; about 25.0 mm across face and 15.0 mm long; with fused corolla tube about 14.0 mm long and 2.5 mm diameter near face and 2.0 mm diameter at base;

Flower aspect: Upright to outwardly;

Flower longevity: About 5 days on plant; self-cleaning;

Flower fragrance: Not detected;

Buds one to two days prior to opening: Narrowly oblanceolate, to narrowly clavate; bluntly acute apex with rounded base; petals implicate; about 16.0 mm long, 8.0 mm long in terminal bulb portion and 8.0 mm long in tube; corolla tube to 2.0 mm diameter, bulb to 3.5 mm diameter;

Bud color: Exposed petal bulb portion nearest RHS N81C; between tube and bulb nearest RHS N92A, corolla tube basal 1.0 mm nearest RHS 145C and distal tube nearest RHS 76B; calyx nearest RHS 137B with strong blushing proximally of nearest RHS 187A;

Petals: Five; consisting of limb and basal claw fused into corolla tube; apex rounded, lightly erose and emarginate, cleft to about 2.0 mm deep; limbs imbricate only at base; limb glabrous adaxial and abaxial, tube puberulent adaxial and glabrous abaxial;

Petal size: Limb about 11.5 mm long and 9.0 mm wide near middle; corolla tube about 14.0 mm long and 2.5 mm diameter at face and 2.0 mm diameter at base;

Petal color upon first opening:

*Adaxial*.—Limb between RHS N80A and RHS N80B with two bars about 1.0 mm long and 0.5 mm wide in center eye nearest RHS N81A; proximal 3.0 mm of corolla tube nearest RHS 145D, remaining distal tube portion between RHS N82C and RHS N82D.

*Abaxial*.—Limb nearest RHS N80B; proximal 3.0 mm of corolla tube nearest RHS 145D, distally nearest RHS N82D.

Petal color upon maturity:

*Adaxial*.—Limb nearest RHS N80A with center fading to nearest RHS 86C; proximal 3.0 mm of corolla tube nearest RHS 145D, remaining distal tube portion between RHS N82C and RHS N82D.

*Abaxial*.—Limb nearest RHS 86C; proximal 3.0 mm of corolla tube nearest RHS 145D, distally nearest RHS N82D.

Androecium: typically five;

*Filaments*.—Typically five, adnate to inner corolla to various heights about 7.0 mm to 11.0 mm from base; free in the distal 0.5 mm to 1.0 mm long and 0.2 mm in diameter; color nearest RHS NN155C.

*Anther*.—Five; oblong elliptic; basifixed; oblong, about 1.5 mm long by 0.7 mm wide; color nearest RHS 17B.

*Pollen*.—Nearly microscopic; color nearest RHS N25D.

Gynoecium: one pistil per flower; 12.0 mm long;

*Style*.—Cylindrical; about 9.5 mm long and 0.2 mm diameter when flower is mature; persistent after flower abscission; color nearest RHS 1D.

*Stigma*.—Trifid in proximal 1.0 mm long, about 0.2 mm diameter; color nearest RHS 1D.

*Ovary*.—Inferior; conical; glabrous; lustrous; slightly acute apex and truncate base; about 1.5 mm long and 1.0 mm diameter; color nearest RHS 144A.

Calyx: Campanulate; pubescent abaxial, glabrous adaxial; about 8.0 mm long and 4.0 mm across at apex;

Sepals: Five; linear to lanceolate; glabrous adaxial and puberulent abaxial; narrowly acute apex, fused in basal 3.0 mm; margin entire; matte abaxial, and lustrous adaxial; individually about 8.0 mm long and 1.0 mm wide at fusion;

Sepal color: Adaxial and abaxial nearest RHS 138A with margins of nearest RHS 157A;

Peduncle: Puberulent; strong, flexible; mostly upright; cylindrical; to about 1.5 mm diameter at base and 2.2 cm long; with average 4.2 flowers;

Peduncle color: Low light or ventrally between RHS 146D and RHS 145B; high light or dorsally nearest RHS 187B;

Pedicle: Cylindrical; puberulent; flexible; upright to outwardly; variable lengths from about 9.0 mm to 5.0 mm long and 0.5 mm diameter;

Pedicle color: Variable depending on light exposure; with low light or ventrally nearest RHS 138A; high light or dorsally nearest RHS N186C;

Fruit and seeds: Not observed;

Hardiness and culture: The new plant grows best with full sun, light moisture and deep drainage; hardy to at least from USDA zone 4 through 8.

Disease and pest resistance: *Phlox* 'Rose Quartz' demonstrates excellent powdery mildew resistance under conditions that would normally show symptoms.

I claim:

1. A new and distinct cultivar of Hybrid Creeping *Phlox, Phlox* plant named 'Rose Quartz', as herein described and illustrated.

* * * * *